United States Patent
Fuh et al.

(10) Patent No.: US 12,383,207 B2
(45) Date of Patent: Aug. 12, 2025

(54) METHOD FOR DETERMINING PROBABILITY OF SUBJECT WITH MILD COGNITION IMPAIRMENT DEVELOPING ALZHEIMER'S DISEASE WITHIN PREDETERMINED TIME PERIOD

(71) Applicants: National Yang Ming Chiao Tung University, Taipei (TW); Taipei Veterans General Hospital, Taipei (TW)

(72) Inventors: Jong-Ling Fuh, Taipei (TW); Albert Chihchieh Yang, Taipei (TW); Shih-Yu Fang, Tainan (TW)

(73) Assignees: NATIONAL YANG MING CHIAO TUNG UNIVERSITY, Taipei (TW); TAIPEI VETERANS GENERAL HOSPITAL, Taipei (TW)

( * ) Notice: Subject to any disclaimer, the term of this patent is extended or adjusted under 35 U.S.C. 154(b) by 358 days.

(21) Appl. No.: 18/309,943

(22) Filed: May 1, 2023

(65) Prior Publication Data
US 2024/0156417 A1    May 16, 2024

(30) Foreign Application Priority Data
Nov. 11, 2022  (TW) .................................. 111143143

(51) Int. Cl.
*A61B 5/00*    (2006.01)
*G06T 7/00*    (2017.01)

(52) U.S. Cl.
CPC .......... *A61B 5/7275* (2013.01); *A61B 5/4088* (2013.01); *A61B 5/7267* (2013.01); *G06T 7/0012* (2013.01); *G06T 2207/10088* (2013.01); *G06T 2207/20076* (2013.01); *G06T 2207/20081* (2013.01); *G06T 2207/30016* (2013.01)

(58) Field of Classification Search
None
See application file for complete search history.

(56) References Cited

U.S. PATENT DOCUMENTS

| | | | |
|---|---|---|---|
| 2005/0215884 A1* | 9/2005 | Greicius | A61B 5/055 600/410 |
| 2011/0046451 A1* | 2/2011 | Horn | G06T 7/0012 382/128 |
| 2014/0236872 A1* | 8/2014 | Keshava | G06N 20/10 706/12 |

* cited by examiner

*Primary Examiner* — Lennin R Rodriguezgonzalez
(74) *Attorney, Agent, or Firm* — Birch, Stewart, Kolasch & Birch, LLP

(57) ABSTRACT

A method is to be implemented by a computing device that stores a risk assessment model, and includes steps of: obtaining an entry of target physiological data and target magnetic resonance imaging (MRI) images of a brain of a subject with mild cognition impairment (MCI); obtaining, based on the target MRI images, voxel values respectively of primitive voxels that are related to grey matter of the brain of the subject; selecting, from among the primitive voxels, any primitive voxel satisfying a filtering criterion as a selected voxel; calculating an average of the voxel value(s) respectively of the selected voxel(s) to obtain an average target voxel value; and obtaining a probability of the subject developing Alzheimer's disease within a predetermined time period by feeding the average target voxel value and the entry of target physiological data into the risk assessment model.

11 Claims, 8 Drawing Sheets

METHOD FOR DETERMINING PROBABILITY OF SUBJECT WITH MILD COGNITION IMPAIRMENT DEVELOPING ALZHEIMER'S DISEASE WITHIN PREDETERMINED TIME PERIOD

CROSS-REFERENCE TO RELATED APPLICATION

This application claims priority to Taiwanese Invention Patent Application No. 111143143, filed on Nov. 11, 2022.

FIELD

The disclosure relates to a method for determining a probability of a subject with mild cognition impairment (MCI) developing Alzheimer's disease (AD) within a predetermined time period.

BACKGROUND

Alzheimer's disease (AD) is a neurodegenerative disease and is the main cause of dementia. AD usually starts slowly and worsens progressively. A patient with AD would gradually lose his/her body functions. Currently, no treatment can stop or reverse the progression of AD, and only some treatments may temporarily improve symptoms caused by AD. In order to help people prepare to confront AD as early as possible, a method for determining a probability of developing AD in the future is demanded.

SUMMARY

Therefore, an object of the disclosure is to provide a method for determining a probability of a subject with mild cognition impairment (MCI) developing Alzheimer's disease (AD) within a predetermined time period.

According to the disclosure, the method is to be implemented by a computing device that stores a risk assessment model. The method includes steps of:
  obtaining an entry of target physiological data that is related to the subject, and a plurality of target magnetic resonance imaging (MRI) images of a brain of the subject;
  obtaining, based on the target MRI images, a plurality of voxel values respectively of a plurality of primitive voxels that are related to grey matter of the brain of the subject;
  selecting, from among the primitive voxels, any of the primitive voxels that satisfies a filtering criterion as a selected voxel;
  calculating an average of the voxel value(s) respectively of the selected voxel(s) to obtain an average target voxel value; and
  obtaining a probability of the subject developing AD within the predetermined time period by feeding the average target voxel value and the entry of target physiological data into the risk assessment model.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
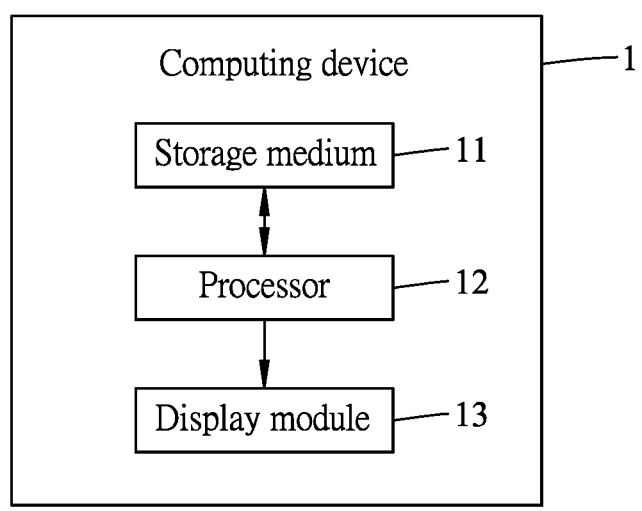
FIG. 1 is a block diagram illustrating a computing device according to an embodiment of the disclosure.

Referring to FIG. 1, an embodiment of a computing device 1 according to the disclosure is illustrated. The computing device 1 may be implemented to be a computing server, a desktop computer, a laptop computer, a notebook computer or a tablet computer, but implementation thereof is not limited to what are disclosed herein and may vary in other embodiments. The computing device 1 includes a storage medium 11, a processor 12 and a display module 13. The processor 12 is electrically connected to the storage medium 11 and the display module 13.

The processor 12 may be implemented by a central processing unit (CPU), a microprocessor, a micro control unit (MCU), a system on a chip (SoC), or any circuit configurable/programmable in a software manner and/or hardware manner to implement functionalities discussed in this disclosure.

The storage medium 11 may be implemented by random access memory (RAM), double data rate synchronous dynamic random access memory (DDR SDRAM), read only memory (ROM), programmable ROM (PROM), flash memory, a hard disk drive (HDD), a solid state disk (SSD), electrically-erasable programmable read-only memory (EEPROM) or any other volatile/non-volatile memory devices, but is not limited thereto.

The display module 13 may be a liquid-crystal display (LCD), a light-emitting diode (LED) display, a plasma display panel, a projection display or the like. However, implementation of the display module 13 is not limited to the disclosure herein and may vary in other embodiments.

The storage medium 11 stores a risk assessment model. The risk assessment model is established by using a machine learning algorithm. In particular, the risk assessment model is established by using a Cox proportional hazards model.

The storage medium 11 further stores a plurality of training data sets that respectively correspond to a plurality of samples (e.g., patients) with mild cognition impairment (MCI). Each of the training data sets contains an observation time interval (e.g., five years) that is related to the corresponding one of the samples, an entry of training physiological data that is related to the corresponding one of the samples and that was obtained at a start time of the observation time interval, a plurality of training magnetic resonance imaging (MRI) images of a brain of the corresponding one of the samples, and an indicator that indicates whether the corresponding one of the samples had developed Alzheimer's disease (AD) at an end time of the observation time interval. It should be noted that the observation time intervals respectively related to the samples may be non-identical (i.e., may not be the same in time length). For each of the training data sets, the entry of training physiological data includes information related to an age of the corresponding one of the samples at the start time of the observation time interval, a medical history of the corresponding one of the samples in aspects of hypercholesterolemia and diabetes, and a score of a mini-mental state examination (MMSE) performed on the corresponding one of the samples.

For example, an entry of training physiological data related to one of the samples (hereinafter referred to as a examinee) and a plurality of training MRI images of a brain of the examinee were obtained on Jan. 1, 2016, the observation time interval corresponding to the examinee is three years, and the indicator corresponding to the examinee indicates that the examinee has not developed AD as of Jan. 1, 2019 (Jan. 1, 2016 and Jan. 1, 2019 are three years apart). In another example, an entry of training physiological data related to another one of the samples (hereinafter referred to as another examinee) and a plurality of training MRI images of a brain of said another examinee were obtained on Jan. 1, 2016, the observation time interval corresponding to said another examinee is two years, and the indicator corresponding to said another examinee indicates that said another examinee has developed AD as of Jan. 1, 2018 (which is two years from Jan. 1, 2016).

Referring to FIGS. 2 to 7, an embodiment of a method for determining a probability of a subject with MCI developing AD within a predetermined time period (e.g., five years) according to the disclosure is illustrated. The method includes a model-establishing procedure and a risk-assessing procedure. In the model-establishing procedure, the risk assessment model is established based on the training data sets. It should be noted that the predetermined time period is not greater than a greatest one among the observation time intervals respectively contained in the training data sets (hereinafter also referred to as a maximum time limit). Moreover, in this embodiment, a plurality of probabilities of the subject developing AD respectively within a plurality of predetermined successive time periods are to be obtained, and a sum of the predetermined successive time periods is not greater than the maximum time limit. In this embodiment, there are five predetermined successive time periods, but a total number of the predetermined successive time periods is not limited to five. For example, the maximum time limit is five years, and the predetermined successive time periods are respectively within a first year, within a second year, within a third year, within a fourth year and within a fifth year.

Figure 2:
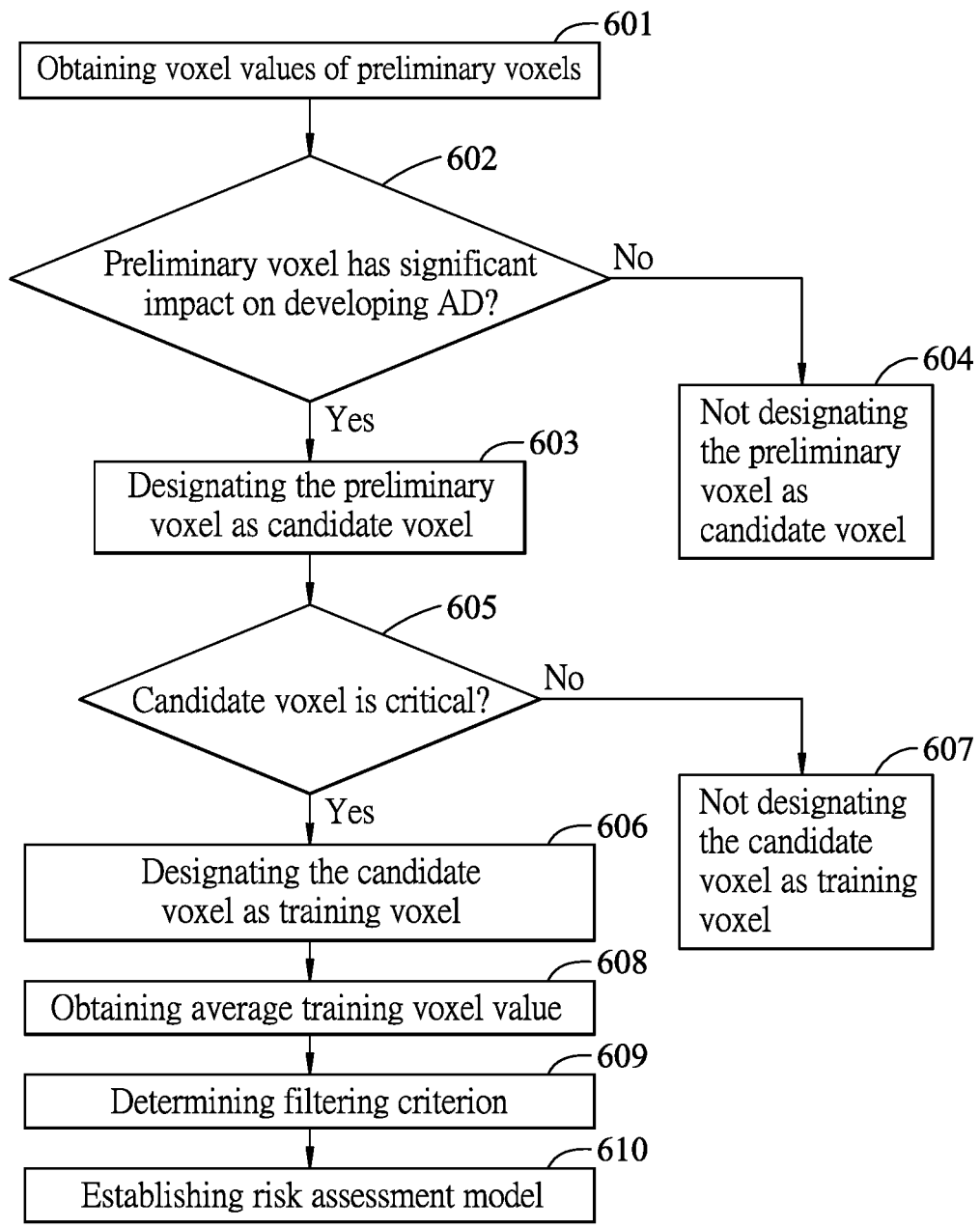
FIGS. 2 to 7 are flow charts cooperatively illustrating a method for determining a probability of a subject with mild cognition impairment (MCI) developing Alzheimer's disease (AD) within a predetermined time period according to an embodiment of the disclosure.

Specifically, referring to FIG. 2, an embodiment of the model-establishing procedure is illustrated. The model-establishing procedure includes steps 601 to 610 delineated below.

It should be noted that steps 601 to 608 are performed with respect to each of the training data sets.

In step 601, the processor 12 of the computing device 1 obtains the entry of training physiological data and the training MRI images, and obtains, based on the training MRI images, a plurality of voxel values respectively of a plurality of preliminary voxels that are related to grey matter of the brain of the corresponding one of the samples.

Figure 3:
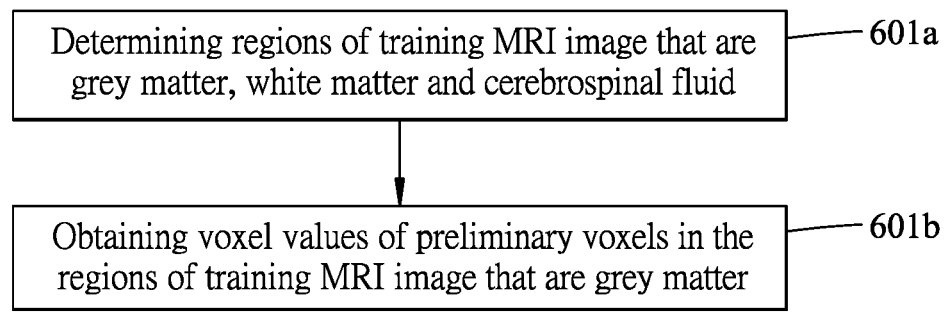

Specifically, referring to FIG. 3, the step of obtaining a plurality of voxel values includes sub-steps 601a and 601b delineated below.

In sub-step 601a, for each of the training MRI images included in the training data set, the processor 12 performs image recognition on the training MRI image to determine a plurality of regions of the training MRI image that are the grey matter, white matter and cerebrospinal fluid of the brain of the corresponding one of the samples.

In sub-step 601b, for each of the training MRI images included in the training data set, the processor 12 performs image analysis on the regions of the training MRI image that are the grey matter to obtain the voxel values respectively of the preliminary voxels.

It should be noted that in practice, sub-steps 601a and 601b are implemented by utilizing a MATLAB toolbox "Data Processing & Analysis for Brain Imaging (DPABI)" with the training MRI images as input.

It should be noted that steps 602 to 604 are performed with respect to each of the preliminary voxels.

In step 602, based on the observation time intervals, the entries of training physiological data and the indicators of the training data sets, and the voxel value of the preliminary voxel thus obtained, the processor 12 determines whether the preliminary voxel has a significant impact on AD development. When it is determined that the preliminary voxel has a significant impact on AD development, a procedure flow of the method proceeds to step 603 to designate the preliminary voxel as a candidate voxel. Otherwise, when it is determined that the preliminary voxel does not have a significant impact on AD development, the procedure flow proceeds to step 604 to not designate the preliminary voxel as a candidate voxel.

Figure 4:
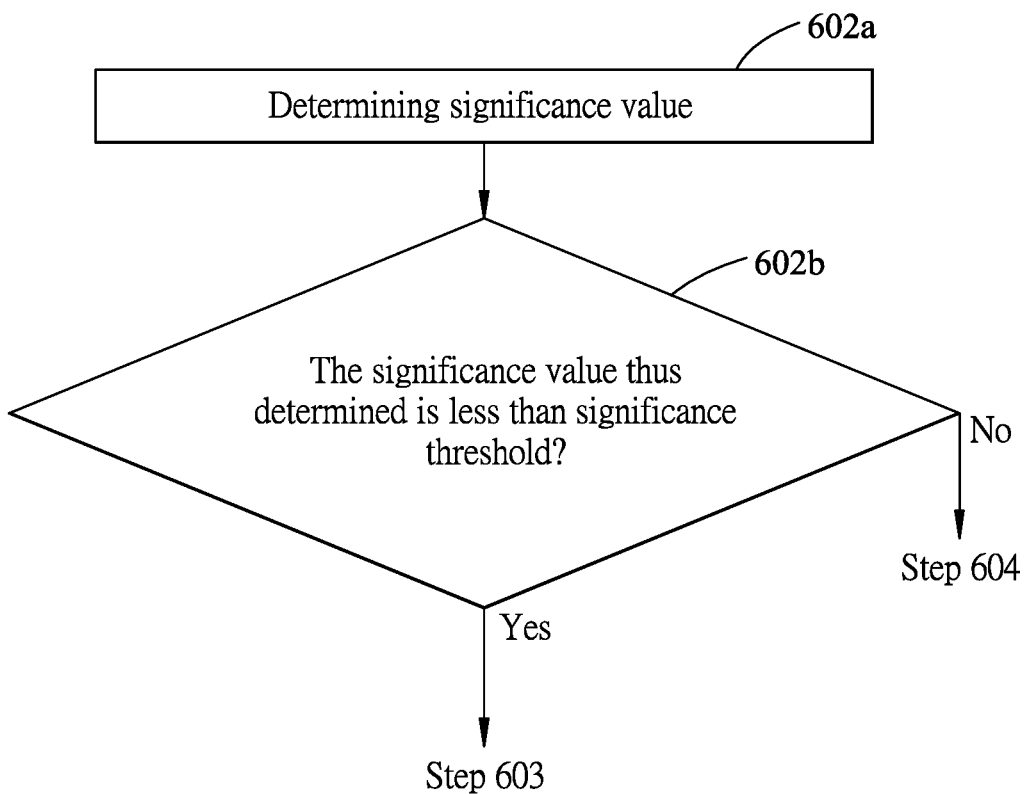

Specifically, referring to FIG. 4, step 602 includes sub-steps 602a and 602b delineated below.

In sub-step 602a, the processor 12 determines a significance value for the preliminary voxel by performing a statistical analysis on the observation time intervals, the entries of training physiological data and the indicators of the training data sets, and the voxel value of the preliminary voxel. In this embodiment, the statistical analysis is Cox survival regression, and the significance value is a p-value obtained by using Cox survival regression.

In sub-step 602b, the processor 12 determines whether the significance value thus determined is less than a significance threshold. The processor 12 determines that the preliminary voxel has a significant impact on AD development when it is determined that the significance value thus determined is less than the significance threshold. The processor 12 determines that the preliminary voxel does not have a significant impact on AD development when it is determined that the significance value thus determined is not less than the significance threshold. The significance threshold is exemplarily 0.05, but is not limited thereto.

Following step 603, steps 605 to 607 are performed with respect to each of the candidate voxels designated in step 603. In step 605, the processor 12 determines whether the candidate voxel is critical based on N number of preliminary voxels that are closest to the candidate voxel, where N is an integer not less than two. In this embodiment, N is exemplarily 125, but is not limited thereto. When it is determined that the candidate voxel is critical, the procedure flow proceeds to step 606 to designate the candidate voxel as a training voxel. On the other hand, when it is determined that the candidate voxel is not critical, the procedure flow proceeds to step 607 to not designate the candidate voxel as a training voxel.

Figure 5:
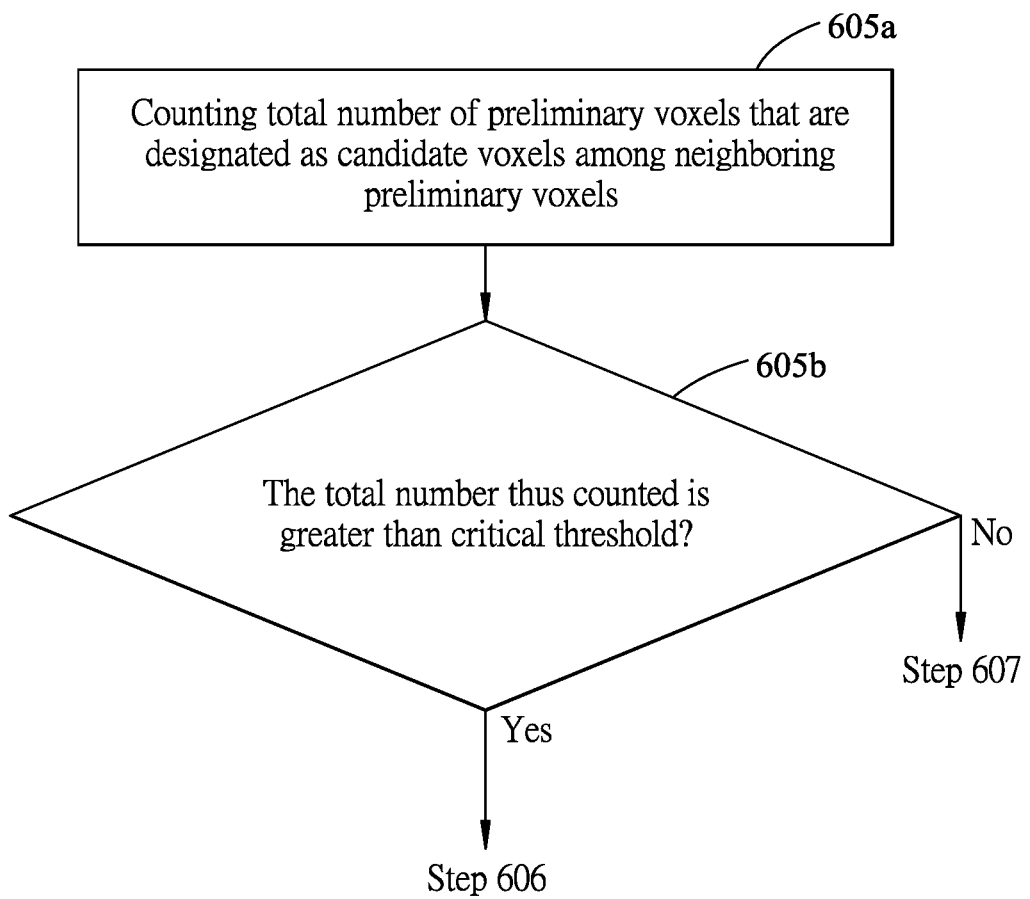

Specifically, referring to FIG. 5, step 605 includes sub-steps 605a and 605b delineated below.

In sub-step 605a, the processor 12 counts a total number of preliminary voxels that are designated as the candidate voxels among the N number of preliminary voxels that are closest to the candidate voxel.

In sub-step 605b, the processor 12 determines whether the total number of preliminary voxels that are designated as the candidate voxels among the N number of preliminary voxels is greater than a critical threshold. The processor 12 determines that the candidate voxel is critical when it is determined that the total number of preliminary voxels that are designated as the candidate voxels among the N number of preliminary voxels is greater than the critical threshold. The processor 12 determines that the candidate voxel is not critical when it is determined that the total number of preliminary voxels that are designated as the candidate voxels among the N number of preliminary voxels is not greater than the critical threshold. The critical threshold is exemplarily 63, but is not limited thereto.

Following step 606, in step 608, the processor 12 calculates an average of the voxel values of all of the training voxels that are designated in step 606 (with respect to all of the preliminary voxels), so as to obtain an average training voxel value.

In step 609, the processor 12 determines a filtering criterion based on the training voxels for all of the training data sets. In this embodiment, the filtering criterion includes positions respectively of the training voxels that are designated in step 606.

In step 610, the processor 12 establishes, by using a machine learning algorithm (i.e., a Cox proportional hazards model), the risk assessment model based on the entries of training physiological data, the observation time intervals and the indicators that are contained in the training data sets, and the average training voxel values for all training data sets. It is worth to note that the risk assessment model is established by using the average training voxel values, which are related to the training voxels that are determined to have significant impact on AD development, so accuracy of determination made by using the risk assessment model may be ensured.

Figure 6:
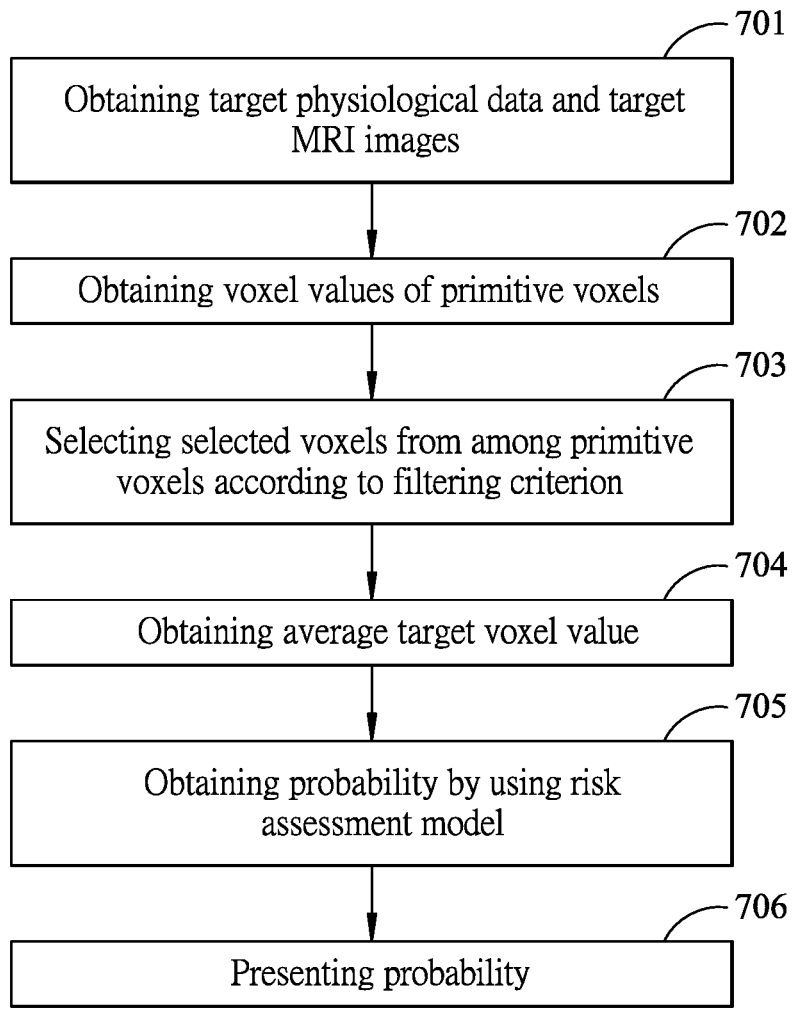

Referring to FIG. 6, an embodiment of the risk-assessing procedure is illustrated. The risk-assessing procedure includes steps 701 to 706 delineated below.

In step 701, the processor 12 obtains an entry of target physiological data that is related to the subject, and a plurality of target MRI images of a brain of the subject. The entry of target physiological data includes information related to an age of the subject, a medical history of the subject in aspects of hypercholesterolemia and diabetes, and a score of an MMSE performed on the subject. It should be noted that the way of obtaining the entry of target physiological data and the target MRI images may be implemented by receiving the same through a wired or wireless communication network from a source terminal (e.g., a database server, not shown), or by receiving the same from an external storage device (e.g., a flash drive, not shown) that is electrically connected to the computing device 1, but is not limited to what are disclosed herein and may vary in other embodiments.

In step 702, the processor 12 obtains, based on the target MRI images, a plurality of voxel values respectively of a plurality of primitive voxels that are related to grey matter of the brain of the subject.

Figure 7:
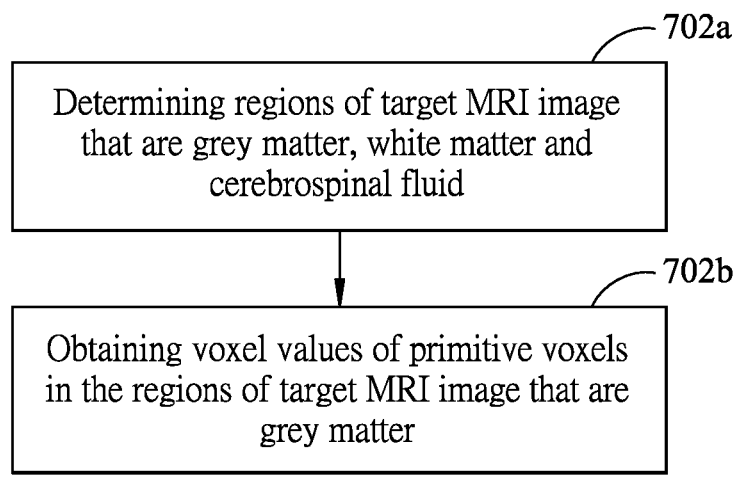

Specifically, referring to FIG. 7, step 702 includes substeps 702a and 702b delineated below.

In sub-step 702a, for each of the target MRI images, the processor 12 performs image recognition on the target MRI image to determine a plurality of regions of the target MRI image that are the grey matter, white matter and cerebrospinal fluid of the brain.

In sub-step 702b, for each of the target MRI images, the processor 12 performs image analysis on the regions of the target MRI image that are the grey matter to obtain the voxel values respectively of the primitive voxels.

It should be noted that in practice, sub-steps 702a and 702b are implemented by utilizing a MATLAB toolbox "Data Processing & Analysis for Brain Imaging (DPABI)" with the target MRI images as input.

In step 703, the processor 12 selects, from among the primitive voxels, any of the primitive voxels that satisfies the filtering criterion (i.e., is located at a position corresponding to any one of the positions included in the filtering criterion) determined in step 609 as a selected voxel.

In step 704, the processor 12 calculates an average of the voxel value(s) respectively of the selected voxel(s), so as to obtain an average target voxel value.

In step 705, the processor 12 obtains the plurality of probabilities of the subject developing AD respectively within the plurality of predetermined successive time periods by feeding the average target voxel value and the entry of target physiological data into the risk assessment model.

Figure 8:
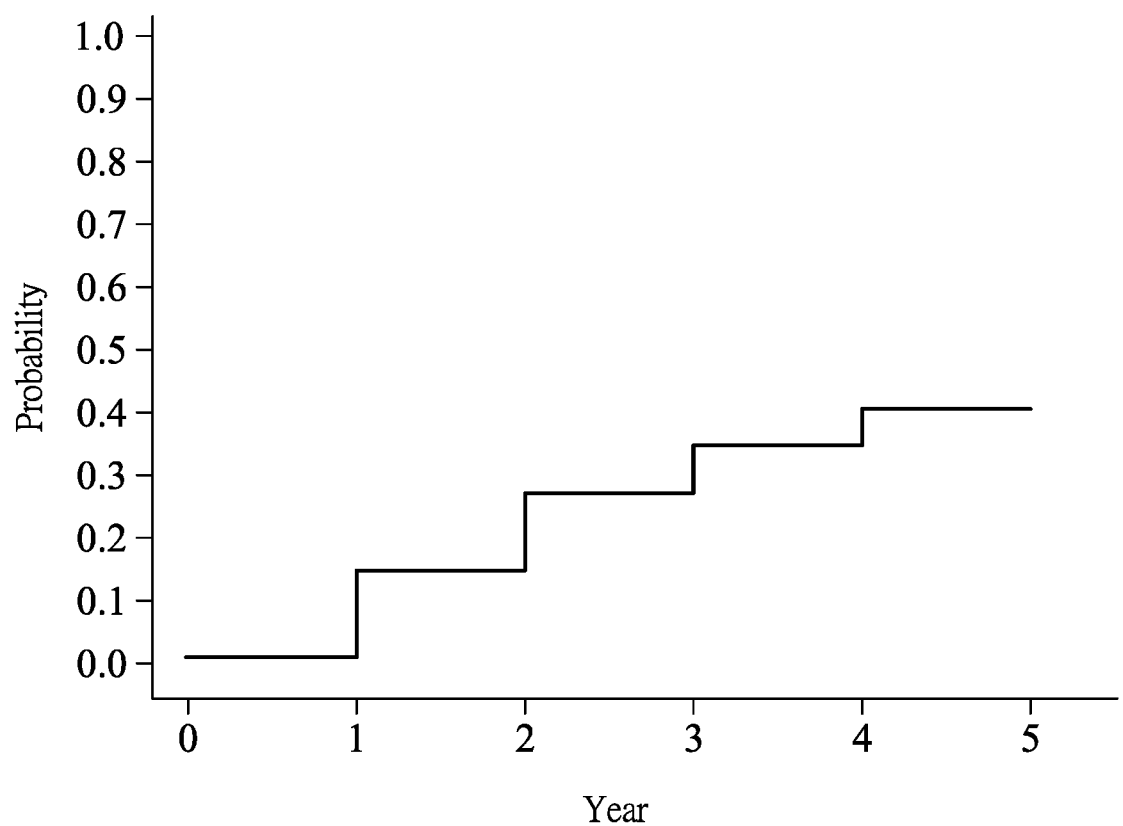
FIG. 8 is a line chart illustrating probabilities of a subject developing AD respectively within predetermined successive time periods.

In step 706, the processor 12 presents, via the display module 13, the probabilities of the subject developing AD respectively within the predetermined successive time periods in a form of a curve graph (e.g., a line chart exemplarily shown in FIG. 8) where a curve is plotted to express the probabilities against the predetermined successive time periods. Particularly, the curve graph includes a horizontal axis that represents time and a vertical axis that represents probability. In this way, a medical practitioner is able to view the curve graph to assess a health condition of the subject. For example, in a scenario where the entry of target physiological data and the target MRI images correspond to a health condition of the subject on Dec. 31, 2021, the processor 12 may utilize the risk assessment model to obtain five probabilities of the subject developing AD respectively within five successive years (i.e., years 2022, 2023, 2024, 2025 and 2026).

To sum up, for the method according to the disclosure, the computing device 1 derives an average target voxel value from target MRI images of a brain of a subject with MCI, and feeds into the risk assessment model the average target voxel value and an entry of target physiological data that is related to the subject so as to obtain a probability of the subject developing AD within a predetermined time period. When multiple probabilities of the subject developing AD respectively within multiple predetermined successive time periods are obtained, the computing device 1 presents the probabilities in a form of a curve graph. In this way, people may be able to prepare to deal with issues related to AD and/or to prevent the onset of AD.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for determining a probability of a subject with mild cognition impairment (MCI) developing Alzheimer's disease (AD) within a predetermined time period, the method to be implemented by a computing device that stores a risk assessment model, the method comprising steps of:
   obtaining an entry of target physiological data that is related to the subject, and a plurality of target magnetic resonance imaging (MRI) images of a brain of the subject;
   obtaining, based on the target MRI images, a plurality of voxel values respectively of a plurality of primitive voxels that are related to grey matter of the brain of the subject;
   selecting, from among the primitive voxels, any of the primitive voxels that satisfies a filtering criterion as a selected voxel;
   calculating an average of the voxel value(s) respectively of the selected voxel(s) to obtain an average target voxel value; and
   obtaining the probability of the subject developing AD within the predetermined time period by feeding the average target voxel value and the entry of target physiological data into the risk assessment model.

2. The method as claimed in claim 1, prior to the step of obtaining a plurality of voxel values respectively of a plurality of primitive voxels, the method further comprising a step of:
   for each of the target MRI images, performing image recognition on the target MRI image to determine a plurality of regions of the target MRI image that are the grey matter of the brain.

3. The method as claimed in claim 1, wherein, in the step of obtaining an entry of target physiological data, the entry of target physiological data includes information related to an age of the subject, a medical history of the subject in aspects of hypercholesterolemia and diabetes, and a score of a mini-mental state examination (MMSE) performed on the subject.

4. The method as claimed in claim 1, the computing device further storing a plurality of training data sets that respectively correspond to a plurality of samples with MCI, each of the training data sets containing an observation time interval that is related to the corresponding one of the samples, an entry of training physiological data that is related to the corresponding one of the samples and that was obtained at a start time of the observation time interval, a plurality of training MRI images of a brain of the corresponding one of the samples, and an indicator that indicates whether the corresponding one of the samples had developed AD at an end time of the observation time interval, the method further comprising steps of:
   for each of the training data sets,
      obtaining, based on the training MRI images, a plurality of voxel values respectively of a plurality of preliminary voxels that are related to grey matter of the brain of the corresponding one of the samples,
      for each of the preliminary voxels,
         based on the observation time intervals, the entries of training physiological data and the indicators of the training data sets, and the voxel value of the preliminary voxel thus obtained, determining whether the preliminary voxel has a significant impact on AD development, and
         designating the preliminary voxel as a candidate voxel when it is determined that the preliminary voxel has a significant impact on AD development,
         determining whether the candidate voxel thus designated is critical based on N number of preliminary voxels that are closest to the candidate voxel, where N is an integer not less than two, and
         designating the candidate voxel as a training voxel when it is determined that the candidate voxel is critical, and
      calculating an average of the voxel values of the training voxels thus designated in the step of designating the candidate voxel as a training voxel performed with respect to all of the preliminary voxels included in the training data set, so as to obtain an average training voxel value;
   determining the filtering criterion based on the training voxels for all of the training data sets; and
   establishing, by using a machine learning algorithm, the risk assessment model based on the entries of training physiological data, the average training voxel values, the observation time intervals and the indicators that are contained in the training data sets.

5. The method as claimed in claim 4, further comprising, prior to the step of obtaining a plurality of voxel values respectively of a plurality of preliminary voxels, a step of:
   for each of the training MRI images included in each of the training data sets, performing image recognition on the training MRI image to determine a plurality of regions of the training MRI image that are the grey matter of the brain of the corresponding one of the samples.

6. The method as claimed in claim 4, wherein the step of determining whether the preliminary voxel has a significant impact on AD development is to:
   determine a significance value of the preliminary voxel by performing a statistical analysis on the observation time intervals, the entries of training physiological data and the indicators of the training data sets, and the voxel value of the preliminary voxel;
   determine whether the significance value thus determined is less than a significance threshold; and
   determine that the preliminary voxel has a significant impact on AD development when it is determined that the significance value thus determined is less than the significance threshold.

7. The method as claimed in claim 4, wherein the step of determining whether the candidate voxel is critical is to:
   count a total number of preliminary voxels that are designated as the candidate voxels among the N number of preliminary voxels that are closest to the candidate voxel;
   determine whether the total number of preliminary voxels that are designated as the candidate voxels among the N number of preliminary voxels is greater than a critical threshold; and determine that the candidate voxel is critical when it is determined that the total number of preliminary voxels that are designated as the candidate voxels among the N number of preliminary voxels is greater than the critical threshold.

8. The method as claimed in claim 4, wherein the step of establishing the risk assessment model is to establish the risk assessment model by using a Cox proportional hazards model.

9. The method as claimed in claim 4, wherein for each of the training data sets, the entry of training physiological data includes information related to an age of the corresponding one of the samples at the start time of the observation time interval, a medical history of the corresponding one of the samples in aspects of hypercholesterolemia and diabetes, and a score of a mini-mental state examination (MMSE) performed on the corresponding one of the samples.

10. The method as claimed in claim 1, wherein the step of obtaining the probability of the subject developing AD within the predetermined time period is to obtain a plurality of probabilities of the subject developing AD respectively within a plurality of predetermined successive time periods.

11. The method as claimed in claim 10, further comprising a step of:
   presenting the probabilities of the subject developing AD respectively within the predetermined successive time periods in a form of a curve graph where a curve is plotted to express the probabilities against the predetermined successive time periods.

* * * * *